(12) United States Patent
Horber

(10) Patent No.: US 7,108,719 B2
(45) Date of Patent: *Sep. 19, 2006

(54) JOINT PROSTHESIS

(76) Inventor: Willi Horber, Turbinenstrasse 12, CH-8005, Zürich (CH)

( * ) Notice: Subject to any disclaimer, the term of this patent is extended or adjusted under 35 U.S.C. 154(b) by 390 days.

This patent is subject to a terminal disclaimer.

(21) Appl. No.: 10/438,970

(22) Filed: May 16, 2003

(65) Prior Publication Data

US 2004/0030394 A1 Feb. 12, 2004

Related U.S. Application Data

(63) Continuation of application No. PCT/CH01/00675, filed on Nov. 16, 2001.

(30) Foreign Application Priority Data

Nov. 16, 2000 (CH) .................................... 2234/00

(51) Int. Cl.
*A61F 2/40* (2006.01)
*A61F 2/30* (2006.01)
*A61F 2/32* (2006.01)

(52) U.S. Cl. ................. 623/19.11; 623/22.4; 623/18.11; 623/23.39

(58) Field of Classification Search .. 623/18.11–20.13, 623/23.39, 22.4–22.46
See application file for complete search history.

(56) References Cited

U.S. PATENT DOCUMENTS

| 3,815,157 | A | 6/1974 | Skorecki et al. |
| 4,011,603 | A | 3/1977 | Steffee |
| 4,318,190 | A | 3/1982 | Cortesi |
| 4,528,702 | A | 7/1985 | Frey |
| 5,314,485 | A | 5/1994 | Judet |
| 5,458,649 | A | 10/1995 | Spotorno et al. |
| 5,522,903 | A | 6/1996 | Sokolow et al. |
| 5,702,457 | A | 12/1997 | Walch et al. |
| 5,702,471 | A | 12/1997 | Grundei et al. |
| 5,741,335 | A | 4/1998 | Gerber et al. |
| 5,888,207 | A | 3/1999 | Nieder et al. |
| 6,093,208 | A | 7/2000 | Tian |
| 6,102,951 | A | 8/2000 | Sutter et al. |
| 6,197,063 | B1 | 3/2001 | Dews |
| 6,228,120 | B1 | 5/2001 | Leonard et al. |

FOREIGN PATENT DOCUMENTS

| DE | 195 09 037 C1 | 9/1996 |
| DE | 19548154 | 6/1997 |

(Continued)

OTHER PUBLICATIONS

Search Report for PCT/CH00/00515 dated Jan. 30, 2001 (cited in U.S. Appl. No. 10/088,630.

(Continued)

*Primary Examiner*—David J. Isabella
(74) *Attorney, Agent, or Firm*—Buchanan Ingersoll & Rooney

(57) ABSTRACT

In a joint prosthesis with a base piece for anchoring in the bone, a collar piece articulated thereon and defining a collar axis, and a collar extension on the collar piece situated on the collar axis, an articulation space is formed on the base piece. An articulation head of the collar piece is disposed therein. The joint prosthesis further includes a head cap disposed on the collar extension and at least one pressure piece for pressing the articulation head against the base of the articulation space. The pressure piece and the base piece can be connected. In a joint prosthesis of this kind, the pressure piece includes a pressure disc with a passage opening for the collar extension.

18 Claims, 8 Drawing Sheets

FOREIGN PATENT DOCUMENTS

| | | |
|---|---|---|
| DE | 196 16 059 A1 | 10/1997 |
| EP | 0 024 442 A1 | 8/1979 |
| EP | 0 208 578 A1 | 6/1986 |
| EP | 0 351 545 A1 | 6/1989 |
| EP | 0 532 440 A1 | 3/1993 |
| EP | 0 633 193 A1 | 12/1993 |
| EP | 0 586 335 A1 | 3/1994 |
| EP | 0 669 117 A1 | 8/1995 |
| EP | 0 679 375 | 11/1995 |
| EP | 0 712 617 A1 | 11/1995 |
| EP | 0 884 032 A1 | 6/1997 |
| EP | 0 850 609 | 12/1997 |
| EP | 0 903 128 | 3/1999 |
| EP | 0 963 741 A2 | 5/1999 |
| FR | 2 321 871 | 8/1975 |
| FR | 2 773 469 | 7/1999 |
| WO | WO 98/46172 | 10/1998 |
| WO | WO 99/34756 | 7/1999 |
| WO | WO 00/01327 | 1/2000 |
| WO | WO01/22905 | 9/2000 |

OTHER PUBLICATIONS

Search Reports for PCT/CH01/00676 dated Mar. 11, 2002 and Apr. 16, 2002.

Search Reports for PCT/CH01/00674 dated Feb. 26, 2002 and Jan. 16, 2003.

Search Report for PCT/CH01/00675 dated Feb. 26, 2002.

JOINT PROSTHESIS

CROSS REFERENCE TO RELATED APPLICATIONS

This application claims priority under 35 U.S.C. §119 to Swiss Application 2234/00 filed in Switzerland on Nov. 16, 2000, and as a continuation application under 35 U.S.C. §120 to PCT/CH01/00675 filed as an International Application on Nov. 16, 2001 designating the U.S., the entire contents of which are hereby incorporated by reference in their entireties.

This application is also related to U.S. Pat. No. 6,749,637, entitled "Endoprosthesis For A Shoulder Joint", issued on Jun. 15, 2004; to U.S. patent application Ser. No. 10/438, 836, entitled "An Endoprosthesis For A Shoulder Joint", filed on even date herewith; and to U.S. Patent, entitled "Joint Prosthesis", Ser. No. 6,818,019, issued on Nov. 16, 2004, each of which is hereby incorporated herein by reference in its entirety.

BACKGROUND

1. Field

The invention relates to a joint prosthesis with a head cap articulated in the manner of a ball joint via a collar piece on a base piece for anchoring in the bone.

2. Background Information

From EP-A-0 663 193 a hip joint socket is known which is held by a holding ring in a supporting shell on an anchoring plate fixed on the bone. In order to prevent any rotation of the hip joint socket in the supporting shell, penetration elements are provided in the supporting shell. If the hip joint socket is now pressed into the supporting shell by a setting instrument with the application of force, the penetration elements penetrate the relatively soft plastic material of the hip joint socket. The holding ring is then brought into the correct position to hold the hip joint socket in the supporting shell.

From WO 99/34756 a shoulder prosthesis is known wherein a collar piece is articulated in a hemispherical recess in the shaft piece, the collar piece being pivotable therein in the manner of a ball joint. The collar piece has a hemispherical articulation surface and a conical surface which is eccentric in relation to an axis through the ball center of said articulation surface, said conical surface being intended for the fitting of a joint cap. The collar piece has a bore which is open from the cap side and which has a hemispherical base. A screw with a spherical head introduced into the bore and adapted to be screwed into the shaft piece through an opening in the base of the bore, co-operates with the base. The spherical surfaces of the hemispherical recess in the shaft piece, of the articulation surface on the shaft piece, of the base of the bore and of the screwhead must have the same center point. In addition, each pair of co-operating hollow and solid spherical surfaces must be made very accurately and have the same radius. Minimal deviations from the ideal measurements have the effect that the collar piece cannot be connected sufficiently firmly to the shaft piece in order to reliably prevent unintentional pivoting of the collar piece relatively to the shaft piece during the use of the joint.

From EP-A-0 712 617 a humeral head prosthesis is known wherein an articulation ball connected to a head cap via a shank is articulated on a shaft piece in a cavity with a hollow spherical base. To fix the articulation ball in the cavity, one or more grub screws are provided which can be screwed through the shaft piece against the articulation ball. In one exemplified embodiment, the articulation ball, which is of cut-open C-shape, is pressed together by the grub screw in order to clamp therein the shank which fits in a central bore in the articulation ball. In another exemplified embodiment, a grub screw is provided which can be screwed along the shank axis through the articulation ball and against the cavity base. With this screw the articulation ball is pressed against the opening of the cavity, which opening in this exemplified embodiment has a smaller radius than the spherical radius of the cavity and the articulation ball.

SUMMARY

The invention is directed to a joint prosthesis wherein for the purpose of aligning the position of the head cap, a collar piece pivotable in the manner of a ball joint in relation to the base part anchorable in the bone, on which collar piece the head cap can be fitted, can be immobilized sufficiently securely on the base piece. At the same time, the production costs can be as low as possible and the use of the prosthesis by the surgeon as simple as possible.

In a joint prosthesis with a base piece for anchoring in the bone, a collar piece articulated thereon and defining a collar axis, and a collar extension on the collar piece situated on the collar axis, and a head cap disposed thereon, an articulation device is formed on the base piece in the form of a recess or surface. An articulation head of the collar piece is disposed thereon. The joint prosthesis further includes a head cap disposed on the collar extension and at least one pressure piece for pressing the articulation head against the base of the articulation device. Means are also provided for connecting the pressure piece and the base piece. The base piece and the head cap are selected from a set of different base pieces and head caps for optimal adaptation to the circumstances of the natural joint. If the natural joint socket is also to be replaced, the joint prosthesis additionally comprises an artificial joint socket. According to the invention, in a joint prosthesis of this kind, the pressure piece comprises a pressure disc with a passage opening for the collar extension.

The pressure disc is rotatable or non-rotatable relatively to the base piece about an axis through the passage opening. Rotatability is necessary particularly if the pressure disc is a cap nut. Rotatability is also advantageous if the contact zones between the contact surfaces of the articulation chamber and of the articulation head are not situated on a spherical surface but, for example, on a cylindrical surface or an other only rotationally symmetrical surface. With articulation of this kind it is advantageous for the pressure disc to be rotatable together with the articulation head about the axis of the cylindrical articulation chamber. In this way it is possible to obtain pivotability of the collar piece in the manner of a ball joint relatively to the base piece even if the pressure disc is non-rotatable relatively to the axial body of the articulation head, because it presses, for example, by two parallel edges against the cylindrical surface thereof. Non-rotatability, on the other hand, has the advantage that on the pressing of the pressure disc against the articulation head no rotary forces act thereon so that its position is not changed by the pressing operation.

If the pressure disc is fixed on the base piece so as to be pivotable about an axis transversely of the collar axis, then to block mobility of the collar piece it is only necessary for it to be pressed unilaterally against the base piece. For this purpose, a single screw or a clamping member can be used for example. This screw can thus be disposed at a readily accessible place. The pivot or some other articulation device ensuring the pivotability of the pressure disc is advantageously disposed at a place which has poor accessibility.

The screw-connectability of the pressure disc to the base piece can be obtained by one or more screws which are screwable through the pressure disc into the base piece. These screws are accessible from the side facing the joint, this side remaining exposed during the entire operation and being covered only when the joint cap is fitted on to the collar extension. Screwability can also be obtained by a cap nut which is constructed as a pressure disc with a passage opening or which presses a pressure disc against the base piece.

A cap nut of this kind can also have a bayonet fastening by which it can be connected to the base piece. The pressure disc can also be connected to the base piece by resilient clamping means or be adapted to be clamped on the base piece via a clamping connection, for example a conical clamping, a wedge clamping, by means of a wedge knocked in, or an eccentric lever.

Advantageously, co-operating contact surfaces present on the articulation head and on the pressure disc are so constructed in respect of shape and material that one or more contact zones form between these contact surfaces, in which zones at least one of the contact surfaces is plastically deformable under the action of the pressure forces occurring during the pressing operation. The deformation of the contact surface results in a positive connection between the articulation head and the pressure disc and hence a stable non-pivotable connection of the two co-operating parts. The contact zones are advantageously punctiform or on a continuous or interrupted line between the articulation head and the pressure plate. The small surface area of the contact zones promotes plastic deformation of the participating contact surfaces. The remarks applicable to the contact zones between the articulation head and the pressure disc also apply to the contact zones between the articulation head and the articulation chamber.

Advantageously, the contact zones lie on a spherical surface so that the articulation of the collar piece ensures complete freedom of a ball joint at every point. Advantageously, at least one of the contact surfaces is formed by one or more body edges or one or more body points. The other contact surface can be formed by a smooth or rough spherical surface, or by body edges or points. In order to counteract any rotation of the collar piece in the articulation chamber, for example under the action of the rotary force of a cap nut on the articulation head, such edges are advantageously aligned transversely of a direction of rotation of the collar piece about a collar axis or transversely of the maximum force acting on the collar piece after clamping.

BRIEF DESCRIPTION OF THE DRAWINGS

The invention will now be explained with reference to exemplified embodiments. In the drawings.

DETAILED DESCRIPTION OF THE DRAWINGS

Figure 1:
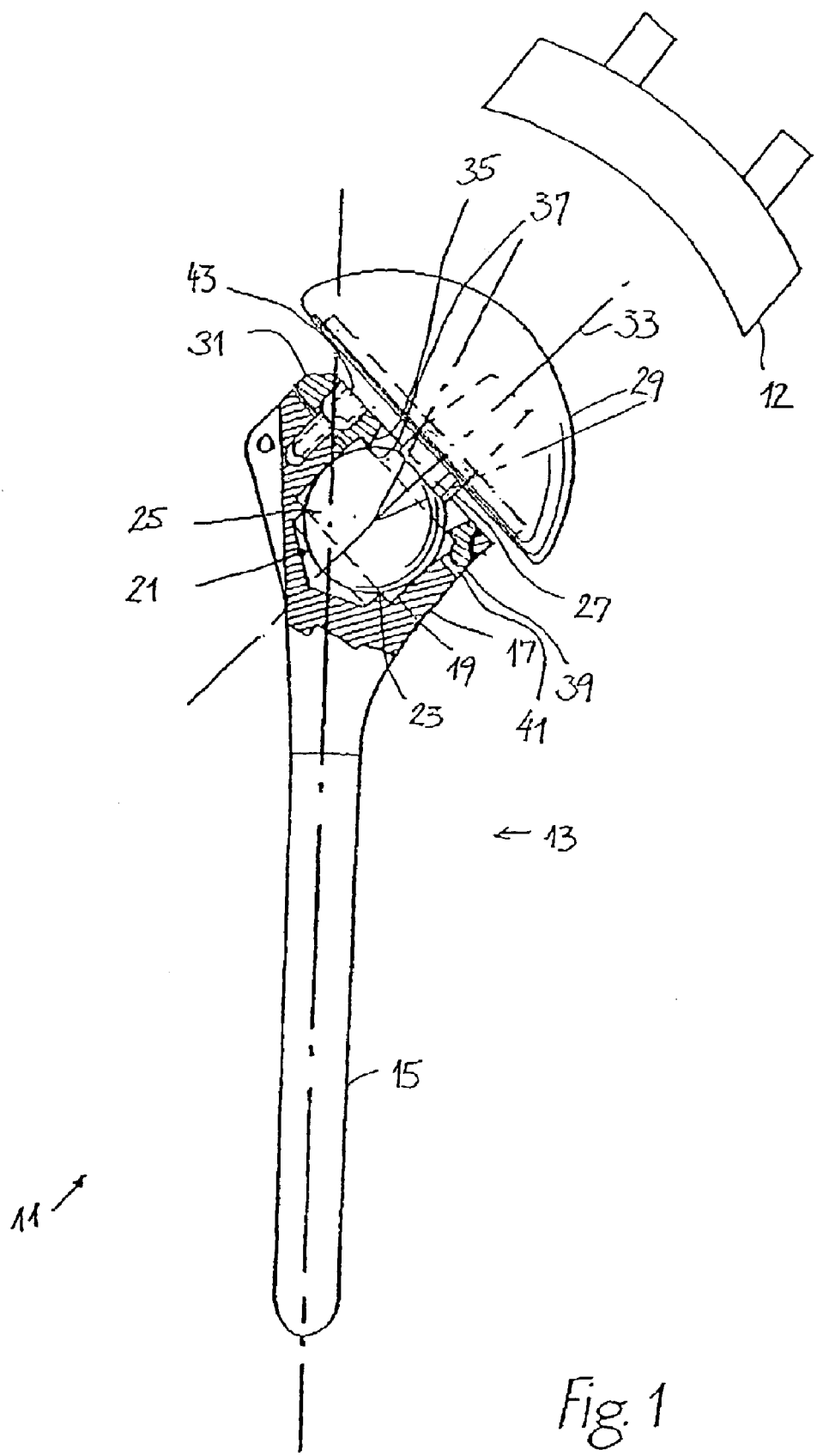
FIG. 1 is a partial section of a shoulder joint prosthesis according to an exemplary embodiment of the invention with a spherical articulation head in an articulation chamber with a circular edge as contact surface.

For the sake of clarity, like and similar parts are given the same reference numerals in the following detailed description of the exemplified embodiments.

The shoulder joint prostheses 11 shown in FIGS. 1 to 9 comprise a base piece or shaft piece 13 for anchoring in the humerus bone of a patient and having a shank 15 and a head 17. An articulation chamber 19 is formed in the shaft head 17. A collar piece 21 is articulated on the shaft piece 13. The collar piece 21 comprises an articulation head 25 bearing in the articulation chamber 19 and a collar extension 27 thereon. A head cap 29 is fitted or is fittable on to the collar extension 27. The collar piece 21 is pressed against the base of the articulation chamber 19 by a pressure disc 31, or by a pressure screw according to FIG. 9. The joint socket is replaced at the same time in some implantation of shoulder joint prostheses. In FIG. 1, the artificial glenoid used in this case is shown diagrammatically and bears the reference 12.

A collar axis 33 is defined by the direction of the collar extension 27. In a central position of the collar piece 21, the collar axis 33 coincides with the axis of the articulation chamber 19. This direction of the collar axis 31 has to be set individually for each patient. To enable the collar axis 33 to be aligned in respect of inclination and anteversion or retroversion, for example perpendicularly to the sectional surface at the patient's bone, the collar piece 21 is mounted after the style of a ball joint in the articulation chamber 19.

The collar axis is thus adapted to be deflected in any direction from the middle position through an angle of about 20°.

FIG. 1 shows a first exemplified embodiment of a shoulder joint prosthesis in which a circular edge 23 at the base of the articulation chamber 19 forms a support for the ball of the articulation head 25. Said circular edge 23 is formed by the orifice edge of a central second bore in the flat base of a first bore in the shaft head 17 forming the main volume of the articulation chamber 19. The larger first bore has a radius corresponding to the spherical radius of the articulation head 25 but may also be larger to facilitate the insertion of the articulation head 25 into the articulation chamber 19. The smaller second bore has a radius corresponding to the circular edge 23. Guidance of the articulation ball 25 is obtained by the two circular edges 23, 37 of the smaller bore and the passage opening 35.

A passage opening 35 for the collar extension 27 is formed in the pressure disc 31. Its diameter may be the same as that of the second bore. The passage opening 35 has a circular opening edge 37 which bears against the articulation head 25. On one side, the pressure disc 31 is articulated by a hinge nose 39 in a hinge recess 41 in the shaft head 17. The hinge nose 39 and hinge recess 41 are adapted to be pushed into one another so that the pressure disc 31 and the shaft piece 13 are releasable from one another. A slot opening can be formed in the pressure disc 31 on the hinge side between two hinge noses so that the pressure disc 31 is horseshoe or C-shaped. On the side opposite the hinge nose the pressure disc 31 is screwed by a screw 43 to the shaft head 17. This gives a three-point clamping between the two hinges 39, 41 and the screw 43.

If the circular edges 23 and 37 bear against the spherical surface of the articulation head 25, without pressure being exerted on the latter, the collar piece 21 is pivotable after the style of a ball joint in relation to the shaft head 17. The screw 43 is tightened to fix the articulation head 25 in the shaft head 17. In this way the two circular edges 23, 37 are moved towards one another. During this, the circular edges 23, 37 are pressed into the spherical surface of the articulation head and subject it to plastic deformation. A very stiff connection is thus obtained between the collar piece 21 and the shaft piece 13 anchorable in the bone.

Figure 2:
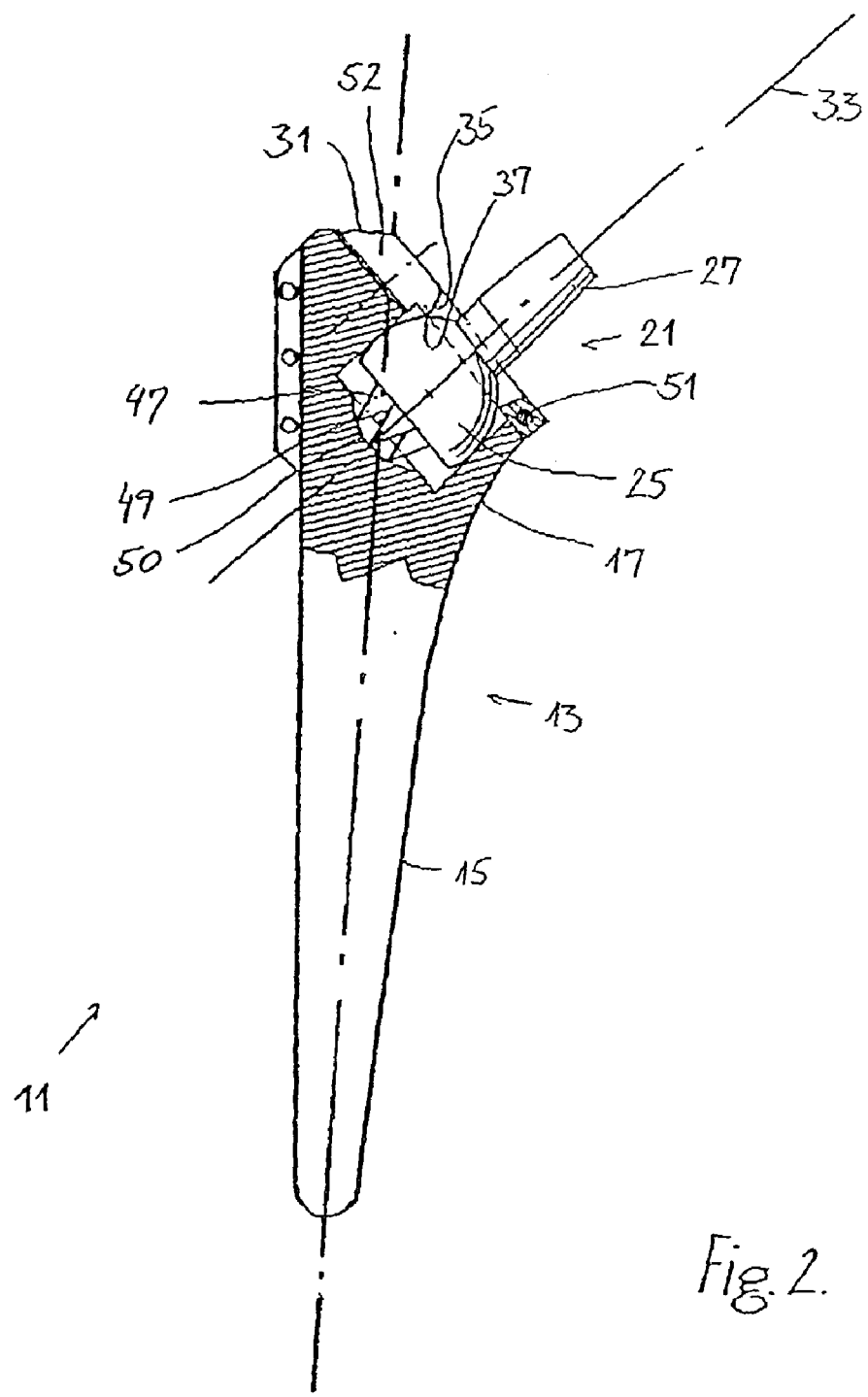
FIG. 2 is a partial section of an exemplary shoulder joint prosthesis without a head cap and with points on the collar piece articulation head, said points being directed against a spherical base of the articulation chamber.

FIG. 2 shows a second exemplified embodiment of a shoulder joint prosthesis 11. The articulation head comprises a spherical surface zone 45 and three pointed members 47. The points 49 of the pointed members 47 are at the same distance from the ball center as the ball surface. The points 49 are directed towards the base of the articulation chamber 19. In the pivoting zone of the points 49 the articulation chamber 19 has a hollow spherical surface 50 with the same radius as the spherical surface of the articulation head 25. The points 49 bear against this hollow spherical surface. The hollow spherical surface 50 is formed in the base of a cylindrical articulation chamber 19. A great circle of the spherical surface of the articulation head 25 bears against the cylindrical generatrix of the articulation chamber 19.

A collar extension 27 extends through a passage opening 35 in a pressure application disc 31. A head cap selected from a set of head caps is fixed on it. The pressure disc 31 is articulated on one side on the shaft head 17 by pivot 51 and is pivotable with respect to the shaft head 17 about the pivot 51. The pressure disc 31 is C-shaped and the C-opening 52 points away from the pivot 51. Thus when the disc 31 is swung up the articulation head 25 can first be introduced into the articulation chamber 19 and then the disc can be swung back. The disc 31 is adapted to be screwed to the shaft head 17 by a screw in each of the two C-limbs (only the axis of the screw is shown). Here, as in the first exemplified embodiment, the passage opening 35 has an opening edge 37 directed towards the articulation head 25 lying in the articulation chamber 19. When the screw 43 is tightened, the articulation head 25 is pressed with this opening edge 37 against the base of the articulation chamber 19. In these conditions, the points 49 of the pointed members 47 dig into the hollow spherical surface 50 of the articulation chamber 19. Depending on the pressure conditions and the materials selected, the opening edge 37 also digs into the spherical surface of the articulation head.

Figure 3:
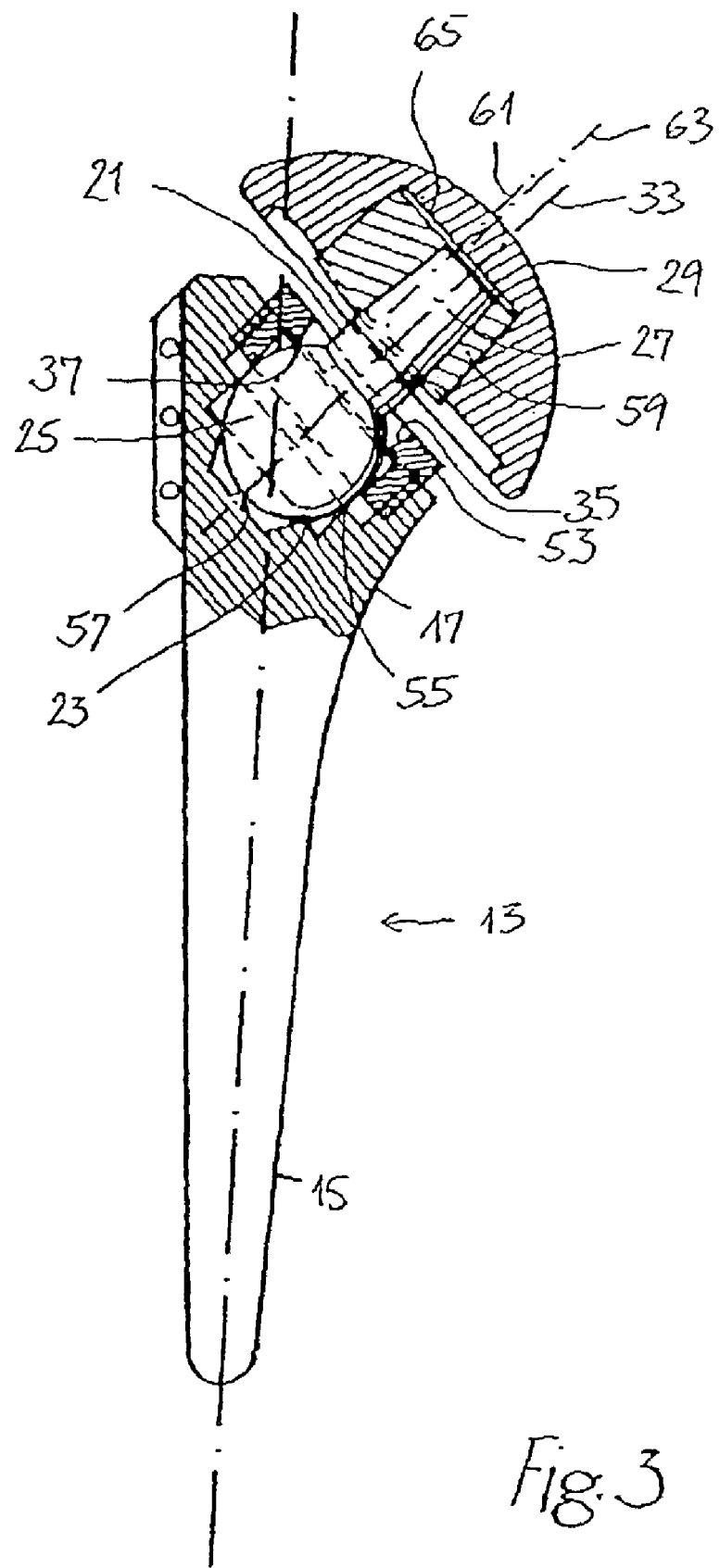
FIG. 3 is a partial section of an exemplary shoulder joint prosthesis with a spherical articulation head and circular edges pressable into the articulation head and also a point of this kind at the base of the articulation chamber.

In the third exemplified embodiment shown in FIG. 3, the pressure piece is formed by a cap nut 53. This is adapted to be screwed into the articulation chamber 19 in a screwthread in the edge of the latter. Like the cap nut in the exemplified embodiment shown in FIGS. 6 and 7, it can also surround the edge of the articulation chamber 19. Here, however, the cap nut also bears against the spherical articulation head 25 along practically a great circle and thus forms a lateral guide for said head. Like the pressure plate 31 in the first two exemplified embodiments, the cap nut engages the articulation head 25 with the opening edge 37 of the passage opening 35 for the collar extension 27.

The cylindrically stepped articulation chamber 19 has a first radius with a screwthread. A smaller second radius has almost the radius of the articulation head 25. The orifice edge of this second hollow cylinder with the second radius forms a first circular edge 55. During the pressing operation the articulation head is pressed into this second hollow cylinder, a clamping fit occurring between the articulation head 25 and the first circular edge 55. A second circular edge 23 with a smaller radius than the first and a point 57 on the axis 33 of the cylindrical bore at the base of the articulation chamber 19 lies approximately on a spherical surface having the same radius as the ball of the articulation head 25. When the articulation head 25 is pressed into the articulation chamber 19, they press into the surface of the articulation head.

FIG. 3 also shows a double eccentric for accurate alignment of the head cap 29 to the contour line of the sectional surface at the bone. The double eccentric is made up of an eccentric ring 59 which is adapted to be pushed on to the collar extension 27, having the axis 61, and a recess 65 disposed eccentrically to the cap axis 63 in the head cap 29 to receive the eccentric ring 59. A clamping fit is provided between the collar extension 29 and the eccentric ring 59, and between the latter and the recess 65. It is necessary to separate the collar piece 21 and the eccentric ring 29 because the eccentric ring 59 does not fit through the passage opening 37. If the collar extension 47 is insertable into the articulation head 25, the eccentric ring 59 can also be made in one piece with the collar extension 57.

Since the invention is independent of the shape of the base piece or shaft piece 13, FIGS. 4 to 9 show only the shaft head 17 with the collar piece 21 and the pressure piece, partly with and partly without eccentric and head cap 29.

Figure 4:
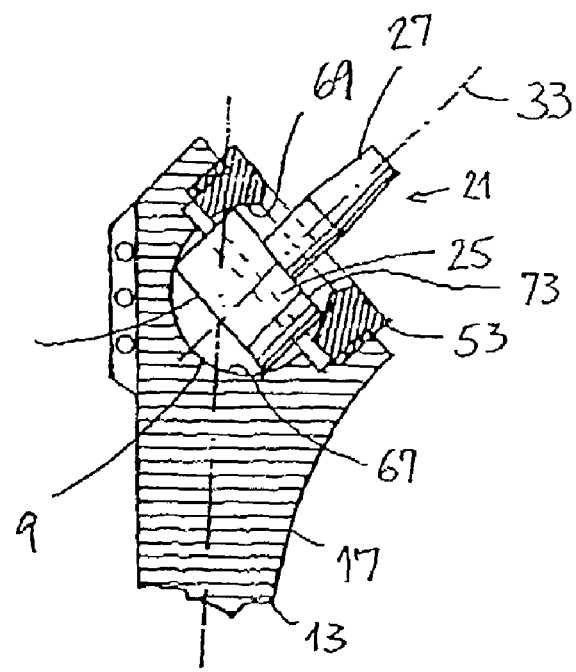
FIG. 4 is a partial section of the head zone of an exemplary shoulder joint prosthesis with a cylindrical articulation head in a spherical articulation chamber.

FIG. 4 shows a fourth exemplified embodiment with an articulation chamber 19 in the shaft head 17 with a substantially hemispherical contact surface 67, a cap nut 53 with a concave, approximately hemispherical contact surface 69, and a collar piece 21 with a cylindrical articulation head 25. The cylindrical articulation head 25 has two circular edges 71, 73 one of which co-operates with the contact surface 67 of the articulation chamber 19 and the other with the contact surface 69 of the cap nut 53. The circular edges 71, 73 are situated on a virtual spherical surface with substantially the same radius as the spherical surfaces 67, 69 of the articulation chamber 19 and the cap screw 53. To adjust the radius of the virtual spherical surface all that is necessary is to change the length of the articulation head 25. The radius of the virtual sphere is advantageously somewhat larger than the radius of the hollow spherical surfaces of the two contact surfaces 67, 69. It is easy to obtain sufficient accuracy of correspondence of the two sphere radii, since the contact surfaces 67, 69 and the circular edges 71, 73 are plastically deformable.

Figure 5:
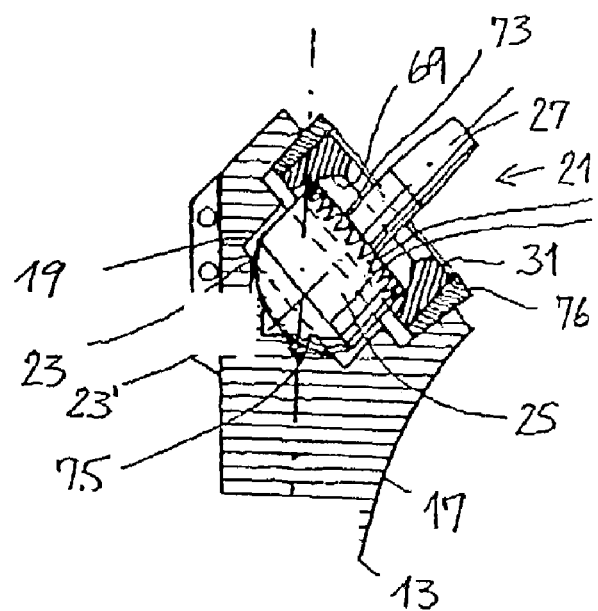
FIG. 5 is a partial section of the head zone of an exemplary shoulder joint prosthesis with circular edges formed at the base of the articulation chamber and in contact with a spherical surface on the articulation head and an interrupted circular line as contact surface between points lying on a circle on the articulation head, and a spherical surface on the pressure piece.

FIG. 5 shows a fifth exemplified embodiment in which the pressure plate 31 is not a cap nut with a screwthread but holds in the shaft head 17 by a clamping fit. It has a hollow spherical contact surface 69 which co-operates with an interrupted circular edge 73 on a partially cylindrical articulation head 25. The circular edge 73 is divided up by incisions in the articulation head 25 to form a series of body points 47, the points 49 of which dig into the contact surface 69 when the articulation disc 31 is knocked into the shaft head 17. The articulation chamber 19 has two circular edges 23, 23' which co-operate with a spherical surface 75 on the articulation head 25. In this exemplified embodiment also, it is relatively easy to obtain correspondence of the radii of the spherical surface 75 and of the circular edge 73 at the articulation head 25, with the radii of the virtual spherical surface on which the circular edges 23, 23' lie and of the contact surface 69 at the pressure disc 61, since the required deformation of the contact zones allows larger tolerances than the pressing of two congruent contact surfaces can. Clamping between the base piece 13 and the pressure disc 31 can be achieved directly by way of a cone. Preferably, however, the clamping of the pressure disc 31 is obtained as illustrated by means of a wedge clamping with, for example, a wedge 76 engaging in the form of a C round the pressure disc.

Figure 6:
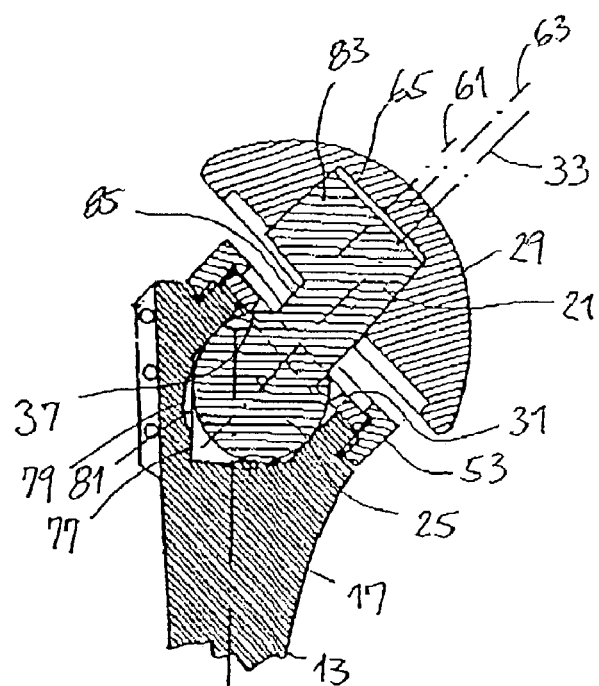
FIG. 6 is a section through the head zone of an exemplary shoulder prosthesis with a spherical articulation head and a conical base of the articulation chamber.

The sixth exemplified embodiment shown in FIG. 6 comprises a conical base 77 for the articulation chamber 19 and a spherical articulation head 25 of the collar piece 21. The generatrix of the base 77 has incisions 79 in the direction of the generatrices through the cone apex. Hence, between the incisions 79 result the formation of edges 81 transversely of a direction of rotation about the axis 33. The pressure disc 31 is fixed on the shaft head 17 by a cap nut 53. The collar piece 21 is integrally equipped with an eccentric 83. The pressure disc 31 is C-shaped. The C-opening has a width which enables a collar zone 85 between the articulation head 25 and the eccentric 83 of the collar piece 21 to be introduced through said C-opening into the passage opening 37 of the pressure disc 31. The cap nut 53 is either also C-shaped or has an opening width which enables the cap nut 53 to be pushed down over the eccentric 83 or up over the articulation head 25 on to the collar piece 21. In the latter case, the cap nut first has to be pushed over the articulation head 25 and then the pressure disc 31 has to be inserted between the articulation head 25 and the cap nut 53. In this example, the articulation disc 31 is rotatable relatively to the cap nut 53. The advantage of this is that on tightening of the cap nut 53 a torque can scarcely be transmitted to the collar piece 21. On the tightening of the cap nut 53 the opening edge 37 is not turned relatively to the articulation head 25 but only pressed against the latter. In the untightened state the collar piece 21 can be turned around the collar axis 33. As a result, the eccentric 83 can be brought into the required position.

Figure 7:
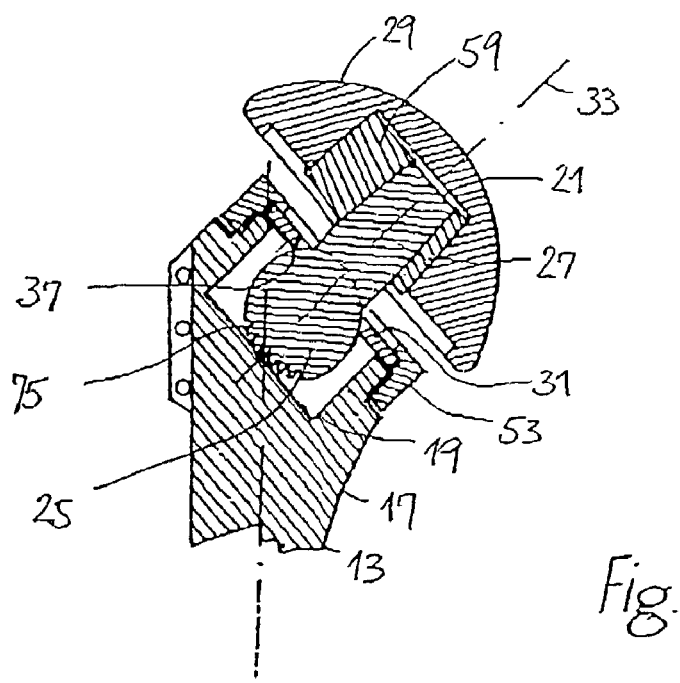
FIG. 7 is a section through the head zone of an exemplary shoulder prosthesis with a cylindrical articulation head with a grooved contact zone in a cylindrical articulation chamber, held by a pressure disc rotatable about the axis of the articulation chamber.

FIG. 7 shows a seventh exemplified embodiment in which the articulation head 25 has a cylindrical shape. The articulation chamber 19 is also cylindrical. The cylindrical axis of the articulation head 25 extends perpendicularly to the collar axis 33, while the cylindrical axis of the articulation chamber 19 is perpendicular to the cylindrical axis of the articulation head 19. The base of the articulation chamber 19 is flat and perpendicular to its cylindrical axis. The radius of the articulation chamber enables the articulation head to turn therein about said cylindrical axis. The pressure disc 31 participates in this rotation each time. It bears by a straight opening edge 37 against the cylindrical surface and is circular. The pressure disc 31 is fixed on the shaft head 17 by a cap nut 53 and is freely rotatable between these parts. As a result the steplessly adjustable deviation of the collar axis 33 from the cylindrical axis of the articulation chamber 19 can be aligned steplessly through 360° perpendicularly to the plane of the bone sectional surface. This gives the same freedom of alignment of the collar axis after the style of a ball joint as a real ball joint. The contact surface 75 of the articulation head 25 facing the base of the articulation chamber 19 is grooved so that edges are formed on the cylindrical surface and dig furrows into the flat base of the articulation chamber 19 on the tightening of the cap nut 53. Both rotation about the cylindrical axis of the articulation chamber 19 and about the cylindrical axis of the articulation head 25 are blocked as a result of this inter-catching of the articulation chamber and the articulation head. In this exemplified embodiment, the pressure disc can also be inserted from the side between the cap nut 53 and the articulation head. The cap nut does not require any screwthread for this purpose, but can be constructed so as to engage in a groove extending around the articulation chamber. Given a wedge shape for the pressure disc and a correspondingly angular contact surface at the cap nut the pressure on the articulation head can be achieved by knocking in the articulation disc.

Figure 8:
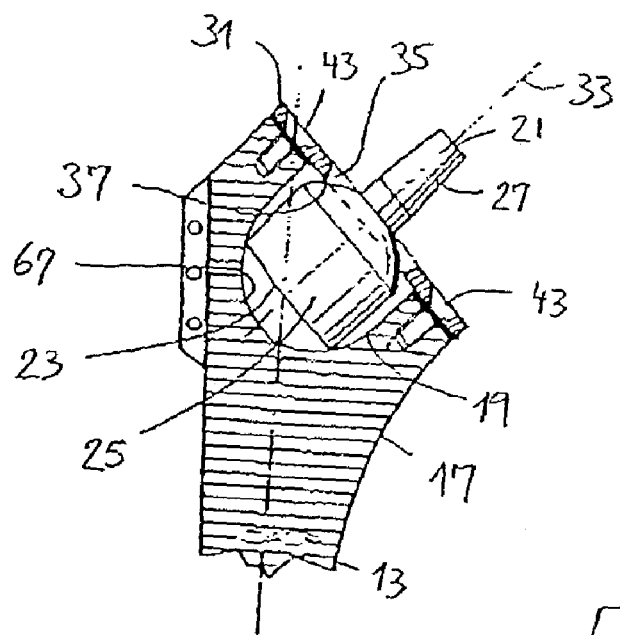
FIG. 8 is a partial section of the head zone of an exemplary shoulder prosthesis with a hemispherical base for the articulation chamber and an articulation head therein which is shaped cylindrically towards said base and which has a spherical surface towards the pressure disc with a circular edge as contact surface.

FIG. 8 shows by reference to an eighth exemplified embodiment a very simple variant of the pressure plate and another possibility of combining cylindrical and spherical members and openings to achieve a connection in the form of a ball joint which has already been constructed a number of times between the articulation chamber and the articulation head and between the shaft head 17 and the collar piece 21. In this example, the articulation chamber has a hemispherical base 67 which co-operates with a circular edge 23 of a cylindrical articulation head 25. Towards the pressure disc 31, however, the articulation head is of spherical construction so that the circular opening edge 37 of the pressure disc 31 bears uniformly against the articulation head in any pivoted position thereof. The pressure disc 31 is adapted to be screwed to the shaft head 17 by two screws 43.

The exemplified embodiments can be modified to the effect that the articulation chamber is formed in the collar piece and the articulation head in the shaft head. The collar extension need not be made integral with the articulation head but can be provided as a shank which can be secured in the articulation head. The construction of the pressure piece is substantially independent of the construction of the articulation surfaces between the articulation chamber and the articulation head, so that the most diverse combinations are possible amongst the embodiment variations shown and mentioned.

Figure 9:
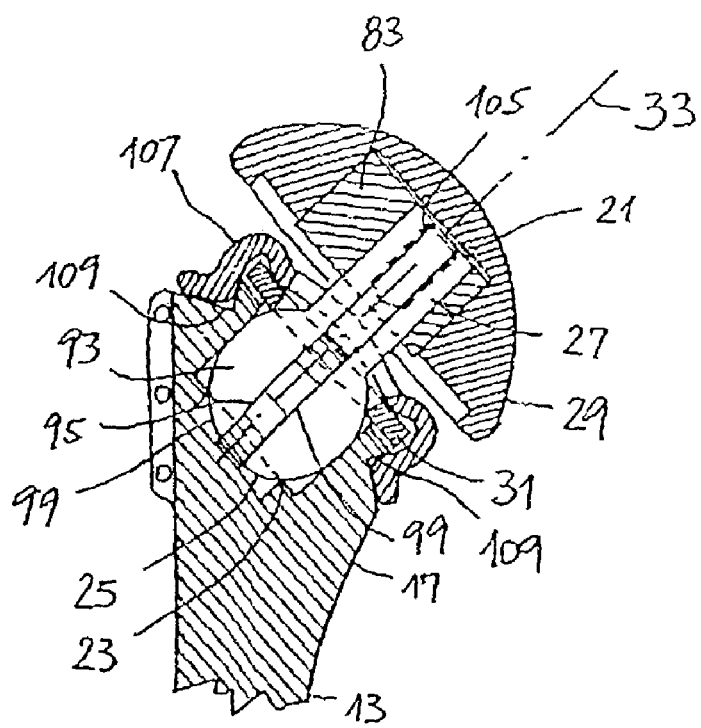
FIG. 9 is a partial section of an exemplary shoulder joint prosthesis with a collar piece according to FIGS. 10 to 12 and a clamping member.

FIG. 9 shows a ninth exemplified embodiment in which the collar piece 21 is made up of two parts 93, 95. Except for the shape of the articulation head 25, the collar piece 21 corresponds exactly to the collar piece 21 shown in FIGS. 10 to 12. The shaft head 17 is provided with a cylindrical articulation chamber 19 in which a body edge 23 is formed against which the edges 99 of the collar piece 21 bear. The collar piece 21 is pressed by a pressure disc 31 against the base of the articulation chamber 19. The force with which the pressure disc 31 is pressed against the shaft 13 is transmitted by a clamping member 107 on to the said disc 31. The clamping member 107 bears against the outside of the pressure disc 31 and engages behind an undercut 109 in the shaft head 17. It is made from a resilient material so that a relatively large force is exerted on the pressure plate. The clamping member 107 can also directly form the pressure disc 31.

Figure 10:
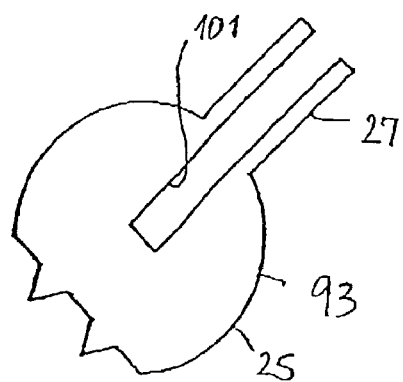
FIGS. 10 and 11 are views of two parts together forming a collar piece.
Figure 11:
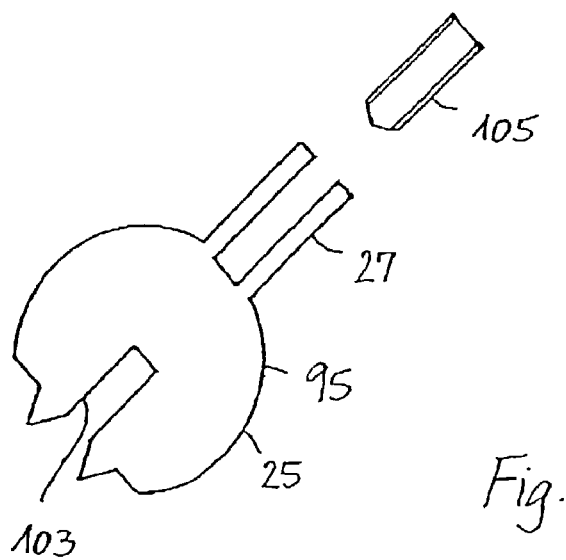
Figure 12:
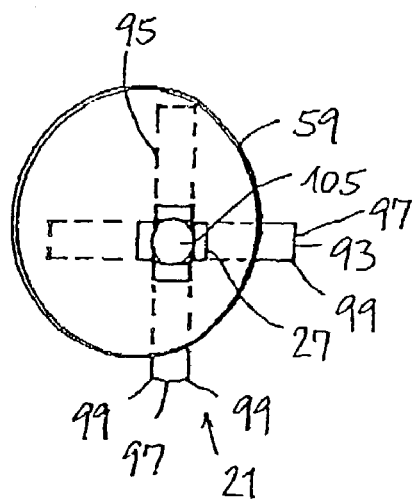
FIG. 12 is a plan view of the collar piece consisting of the parts shown in FIGS. 10 and 11 with an eccentric ring.

As already stated, the articulation head 25 need not be a solid member. It can, for example, as shown in FIGS. 10 to 12, be made up of individual parts. FIGS. 10 and 11 show the elevations of two parts 93 and 95 in the form of plates which can be fitted together. Assembled, the parts 93, 95 form a collar piece 21 which can be used instead of the collar piece 21 in FIG. 2. The parts 93, 95 are simple to produce. For example they can be laser cut from a plate or be cast. The edge surface 97 need not be a spherical surface. As a result of pressing into the articulation chamber the edges 99 are so deformed that there is a large-area contact and also very good toothing between the shaft head 17 and the collar piece 21. The part 93 in FIG. 10 can be pushed with the slot 101 across the slot 103 on the part 95 in FIG. 11 on to said part 95 so that all the edges 99 are situated on a common spherical surface. In the collar extension 27 there is formed in both parts 93, 95 a groove into which a screw 105 can be screwed.

The collar extension 27 comprising the two parts 93, 95 forms a cross with a central square recess. The eccentric ring 59 can be placed on this cross. As a result of the cross shape of the collar extension 27 and a corresponding recess in the eccentric ring, it is impossible for the eccentric ring 59 to turn relatively to the collar piece 21. To fix the eccentric ring 59 on the collar extension 27 and the two parts 93, 95 against one another, the screw 105 can now be screwed in, resulting in clamping between the parts 93, 95 on the one hand and the eccentric ring 59 on the other hand. In FIG. 12, the assembled collar piece 21 with the eccentric ring 59 is shown in plan view. This view shows how the edge surfaces 97 of the two parts are constructed orthogonally to the plate plane.

Figure 13:
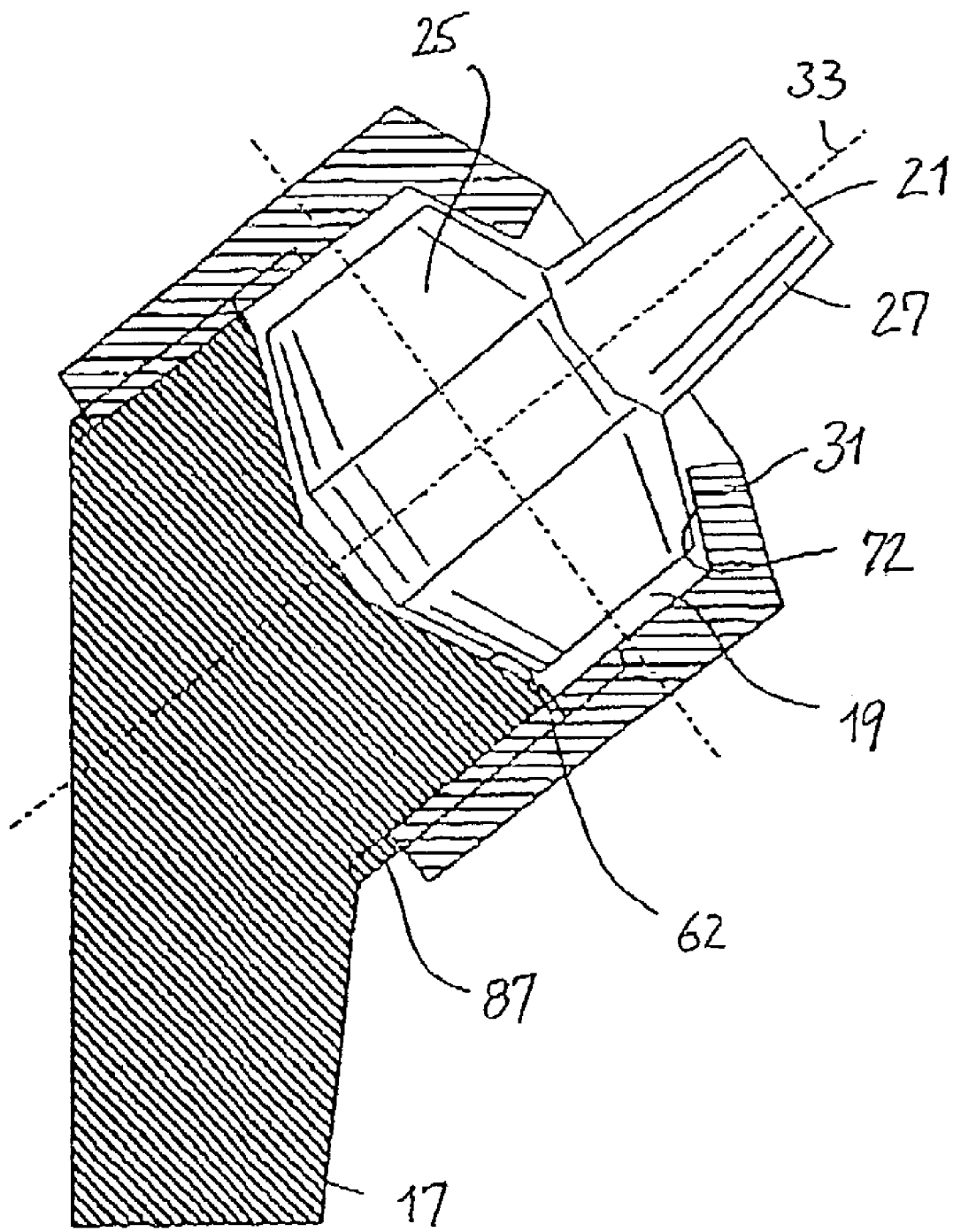
FIG. 13 is a section through the head zone of the shaft piece with an articulation head which is disposed in an articulation chamber formed in a screw-on cover.

FIG. 13 shows an exemplified embodiment wherein the articulation chamber 19 is formed in a cover, which cover is constructed as a cap nut 53 and is screwed on to an external screwthread 87 formed on the shaft head 17. The articulation member 25 has two oppositely directed frusto-conical surfaces acting as articulation surfaces. The base 62 of the articulation chamber 19 is also frusto-conically concave. The two angles of the co-operating cone generatrices correspond to one another complementarily. The clamping plate 31 on the cover 53 also has a frusto-conical clamping surface 72.

The clamping plate 31 can also be in the form of a washer pressed by a cap nut 53 against the articulation member 25. It need not therefore be made integrally with the cap nut. This has the advantage that on the tightening of the cap nut 53 there is less transmission of a turning of the cap nut on to the articulation member 25. The clamping surfaces of the base 62 and/or the clamping plate 31 can also be constructed as one or more complementarily frusto-conically disposed annular edges.

To summarize, in a joint prosthesis 11, the head cap 29 is connected via a collar piece 21 to a base piece 13 for anchoring in the bone. The collar piece 21 is articulated after the style of a ball joint on the base piece 13. For this purpose an articulation head 25 is disposed on the collar piece 21 in an articulation chamber 19 on the base piece 13 and is pressed against the base of the articulation chamber 19 by means of a pressure disc 31. The latter has a passage opening 35 for the collar piece 21.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. A joint prosthesis comprising:
   an artificial joint socket for anchoring in a first bone or for pivotal co-operation with a natural joint socket in the first bone;
   an axial base piece for anchoring in a second bone;
   an articulation head articulated on the axial base piece and forming, together with a collar extension disposed thereon and defining a collar axis, a collar piece which is pivotable and rotatable relative to the base piece about at least two axes passing through the articulation head and perpendicular to one another;
   a head cap disposed on the collar extension and co-operating as a joint with the joint socket;
   at least one pressure piece for pressing the articulation head against the base piece; and
   means for connecting the pressure piece and the base piece so that the collar extension is lockable in a desired selected rotary position and angular position to the axis of the base piece, between the pressure piece and the base piece, wherein the pressure piece comprises a pressure disc with a passage opening for the collar extension.

2. A joint prosthesis according to claim 1, wherein the pressure disc is rotatable relative to the base piece about an axis through the passage opening.

3. A joint prosthesis according to claim 1, wherein the pressure disc is non-rotatable relative to the base piece with respect to an axis through the passage opening.

4. A joint prosthesis according to claim 1, wherein the pressure disc is fixed on the base piece so as to be pivotable about an axis transversely of the collar axis.

5. A joint prosthesis according to claim 1, wherein the pressure disc and base piece are adapted to be screwed together.

6. A joint prosthesis according to claim 5, wherein the pressure disc is a cap nut or is fixable with a cap nut.

7. A joint prosthesis according to claim 6, wherein cap nut is connectable to the base piece by a bayonet fastener.

8. A joint prosthesis according to claim 1, wherein the pressure disc is connectable to the base piece by resilient clamping means.

9. A joint prosthesis according to claim 8, wherein the pressure disc is adapted to be clamped on the base piece via a clamping connection.

10. A joint prosthesis according to claim 1, wherein the pressure disc is annular.

11. A joint prosthesis according to claim 1, wherein the pressure disc is C-shaped.

12. A joint prosthesis according to claim 1, comprising:
    co-operating contact surfaces present on the articulation head and on the pressure disc constructed in respect of shape and material such that at least one contact zone forms between said contact surfaces, in which zone at least one of the contact surfaces is plastically deformable under the pressure forces during pressing.

13. A joint prosthesis according to claim 12, comprising: at least one punctiform contact or one linear contact between the articulation head and the pressure plate.

14. A joint prosthesis according to claim 12, wherein the contact zone lies on a spherical surface.

15. A joint prosthesis according to claim 1, comprising: contact surfaces on the articulation head and in an articulation chamber, constructed such that at least one point contact lying on a spherical surface or a linear contact exists between a clamping surface of the articulation chamber and the articulation head.

16. A joint prosthesis according to claim 15, wherein one of the contact surfaces is formed by one or more body edges or by one or more body points, and another contact surface is formed by a spherical surface.

17. A joint prosthesis according to claim 16, wherein a contact surface co-operating with the spherical surface forms edges which lie transversely of a rotational direction of the collar piece about a collar axis.

18. A joint prosthesis according to claim 17, wherein an articulation chamber is formed in a cover or cap nut which is screwable by an internal screwthread on to an external screwthread on the shaft piece.

* * * * *